(12) United States Patent
Stork et al.

(10) Patent No.: US 6,835,204 B1
(45) Date of Patent: Dec. 28, 2004

(54) INTRAOCULAR LENS HAVING A CENTRAL LENS AREA, AN ANNULAR LENS AREA, AND A MERIDIAN SECTION

(75) Inventors: Wilhelm Stork, Impflingen (DE); Christine F. Kreiner, München (DE)

(73) Assignee: Acri.Tec Gesellschaft fur Ophtalmologische Produkte mbH (DE)

( * ) Notice: Subject to any disclaimer, the term of this patent is extended or adjusted under 35 U.S.C. 154(b) by 17 days.

(21) Appl. No.: 10/009,409

(22) PCT Filed: May 29, 2000

(86) PCT No.: PCT/EP00/04888

§ 371 (c)(1),
(2), (4) Date: Mar. 27, 2002

(87) PCT Pub. No.: WO00/76426

PCT Pub. Date: Dec. 21, 2000

(30) Foreign Application Priority Data

Jun. 10, 1999 (DE) .......................... 199 26 512

(51) Int. Cl.⁷ .................................................. A61F 2/16
(52) U.S. Cl. ...................... 623/6.25; 623/6.23; 623/6.28
(58) Field of Search .............................. 623/6.11, 6.18, 623/6.19, 6.23, 6.24, 6.25, 6.27, 6.29, 6.3, 6.31

(56) References Cited

U.S. PATENT DOCUMENTS 5,054,905 A * 10/1991 Cohen ........................ 351/161
5,121,980 A * 6/1992 Cohen ........................ 351/161
5,225,858 A * 7/1993 Portney ....................... 351/161
5,229,797 A * 7/1993 Futhey et al. ............... 351/161
5,864,379 A * 1/1999 Dunn .......................... 351/161
6,120,148 A * 9/2000 Fiala et al. .................. 351/161

FOREIGN PATENT DOCUMENTS

| EP | 0180887 | 5/1986 | |
| EP | 0276331 | 8/1988 | |
| EP | 0342895 | 11/1989 | |
| EP | 0367878 | 5/1990 | |
| EP | 0458508 | 11/1991 | |
| EP | 537643 A1 * | 4/1993 | ........... A61F/02/16 |

OTHER PUBLICATIONS

English Translation of EP 0276331 A1.*
English Translation of EP 0537643 A1.*
Derwent abstract of EP 537643 A1; Stork et al., Jun.–1993.*
Derwent abstract of EP 276331 A1; Meur, Aug.–1988.*

* cited by examiner

Primary Examiner—David H. Willse
Assistant Examiner—Urmi Chattopadhyay
(74) Attorney, Agent, or Firm—Ostrolenk, Faber, Gerb & Soffen, LLP

(57) ABSTRACT

An intraocular lens with an optical lens part, which has a central lens area and at least one further annular lens area surrounding the central lens area, the central lens area and the at least one annular lens area forming at least one common focus and the annular lens area having concentric annular zones, in which the difference in pathlength between adjacent zones is an integral multiple of n=2 or more of the design wavelength.

14 Claims, 1 Drawing Sheet

INTRAOCULAR LENS HAVING A CENTRAL LENS AREA, AN ANNULAR LENS AREA, AND A MERIDIAN SECTION

BACKGROUND OF THE INVENTION

The invention relates to an intraocular lens having a central lens area and a surrounding annular lens area.

1. Prior Art

An intraocular lens of this type is known from EP 0 537 643 B1. This lens may be designed as a monofocal lens, and consequently be made relatively thin, by the optical power being made up of a refractive component and a diffractive component. The cut to be made to the eye during the implantation can be kept small. Scatterings of light resulting from the diffractive fine structure component may influence the quality of the image produced on the retina.

2. Object of the invention

The object of the invention is to provide an intraocular lens of the type stated at the beginning in which an image with improved quality is produced on the retina with a low lens thickness.

EXAMPLES

This object is achieved according to the invention by an intraocular lens with an optical lens part, which has a central lens area and at least one further annular lens area surrounding said central lens area, the central lens area and the at least one annular lens area forming at least one common focus and the annular lens area having concentric annular zones, in which the difference in pathlength between adjacent zones is an integral multiple of n=2 or more of the design wavelength.

In the case of the intraocular lens according to the invention, arranged around a central lens area, which has refractive properties in particular, is at least one annular lens area, which forms a common focus with the central lens area, concentric annular zones arranged around the optical lens axis being provided in the annular lens area, the difference in the path length or difference in optical path between adjacent zones being an integral multiple of the design wavelength.

In a preferred way, the design wavelength is provided in the green spectral range of visible light, in the range of 550 nm for example.

The difference in path length of the adjacent zones may be set by the refractive index or by appropriate material selection and/or the geometry of the respective zone.

In a preferred way, the curvature of the meridial section of the optical lens part is aspherically formed, the zones with the differences in path length (differences in optical path) being provided in the edge region, in which the deviation of the aspherical profile from the spherical curve has an effect.

These annular zones, which are arranged concentrically around the optical lens axis, are formed in particular in a sawtooth shape. For forming a monofocal intraocular lens, these zones have the same optical power as the central, in particular refractive, lens area. Both parts contribute to a sharp image, which is produced on the retina of the eye.

For forming a bifocal lens, the optical lens part may be provided with an additional diffractive fine structure, which may extend over the entire optical lens part or, in a preferred way, is provided only on the central lens area, forming the refractive component. This is generally sufficient, since the bifocal function is required only when there is brightness corresponding to daylight and the pupillary aperture of the eye is essentially open only in the region of the central lens area, containing the refractive component. The additional diffractive fine structure, in particular in the form of concentric zones arranged around the optical lens axis, may be formed in such a way that adjacent zones produce a difference in path length of the optical path which is a fraction of the design wavelength, for example 0.4 or 0.6.

The invention is explained in more detail on the basis of exemplary embodiments with reference to the figures, in which:

DETAILED DESCRIPTION OF PREFERRED EMBODIMENTS

Figure 1:
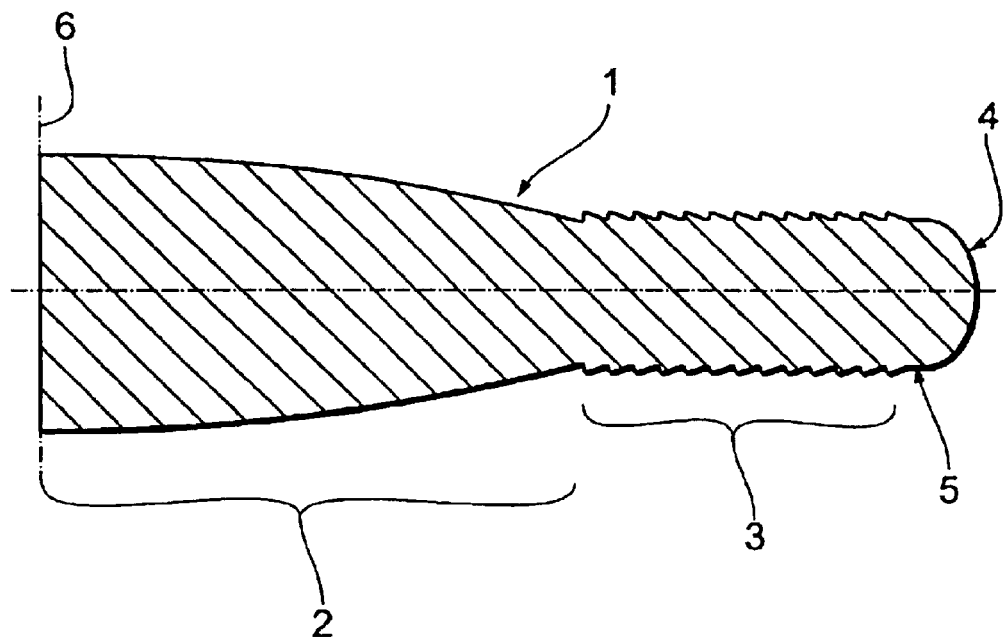
FIG. 1 shows a sectional representation through one half of a lens body of an intraocular lens.

The optical lens part 1, represented in the figures, of an intraocular lens has a central, in particular refractive, lens area 2 and a lens area 3 arranged in an annular form around the central lens area 2. The annular lens area 3 is located in an edge zone of the lens body. In the case of the exemplary embodiment represented, fine structure elements, in particular with a sawtooth shape, are arranged both on the front side and on the rear side of the lens body in concentric zones around the optical axis 6 of the lens part 1. It is also possible, however, to provide the sawtooth-like zones only on one side of the lens (front side or rear side).

Adjacent zones have a difference in path length of the respective optical path which corresponds to an integral multiple of two or more of the design wavelength. By different selection of the material in the respective adjacent annular zones and the associated different refractive indices and/or the geometry, in particular the sawtooth shape, this difference in path length of the respective optical paths can be achieved.

An outer peripheral edge 4 of the lens body has an approximately semicircular cross section, with a radius of 0.165 mm. The semicircular edge begins at a radial distance of approximately 2.835 mm from the optical axis 6. A planar straight piece 5 may be provided between the edge 4 and the annular lens area 3 with the sawtooth-like zones. This is the case in particular whenever the outermost sawtooth zone can no longer be provided completely before the semicircular lens edge 4. The diameter of the lens is approximately 6 mm. In a preferred way, at least three annular sawtooth zones are provided in the annular lens area 3 in the vicinity of the lens edge 4.

The various curve portions are described by various functions in the respective portions.

The optical lens part is described by the following function:

$$Z_{asph}(r) = R - \sqrt{R^2 - r^2} + a_4 \cdot r^4 + a_6 \cdot r^6 + a_8 \cdot r^8 + a_{10} \cdot r^{10} + \ldots$$

if $< r < r_{\text{rfres\_begin}}$

The annular lens area 3 is described by the floor function:

$$z\_fres(r) = z_{asph}(r) - \text{floor}\left[\frac{Z_{asph}(r) - Z_{asph}(r_{\text{fres\_begin}})}{\text{tooth depth}} + 1\right] \cdot \text{tooth depth}$$

if $r_{rdres\_begin} < r < r_{fres\_end}$

The straight piece 5 is described by the straight line:

$$z(r) = Z_{asph}(r_{fres\_begin}) \text{ if } r_{fres\_end} < r < r_{circle\_begin}$$

The edge region is described by a circle function with the radius R=0.165 mm:

$$Z_{circle} = Z_{mpoint} \sqrt{R^2 - (r - \chi_{point})^2} \text{ if } r_{Pmax} < r < r_{max}$$

with $Z_{mpoint}$=Z coordinate of the midpoint of the edge circle, $x_{mpoint}$=r coordinate of the midpoint of the edge circle. $r_{max}$ is the maximum distance from the axis or the half diameter. With the exception of $r_{rfres\_begin}$, the r coordinates of the edge circle are equal in the case of all mold inserts.

In a preferred way, the zones with the differences in path length of the lens area 3 are located in the region of the deviation of the asphere from the spherical curve. The refractive component is formed by the central lens area 2, which in a preferred way has the spherical lens shape.

For forming a monofocal lens, the central lens area 2 and the annular lens area 3 are shaped in such a way that they have exactly the same focus and a common image is produced in all the zones of the optical lens part 1. The differences in the optical path length of the optical paths in adjacent zones are in this case adapted exactly to an integral multiple of an average wavelength of the visible spectrum, in particular to approximately 550 mm (design wavelength). The lens therefore produces a perfect image into the edge region. The depth of the concentric sawtooth zones is reduced here from zone to zone by 0.3 µm.

Figure 2:
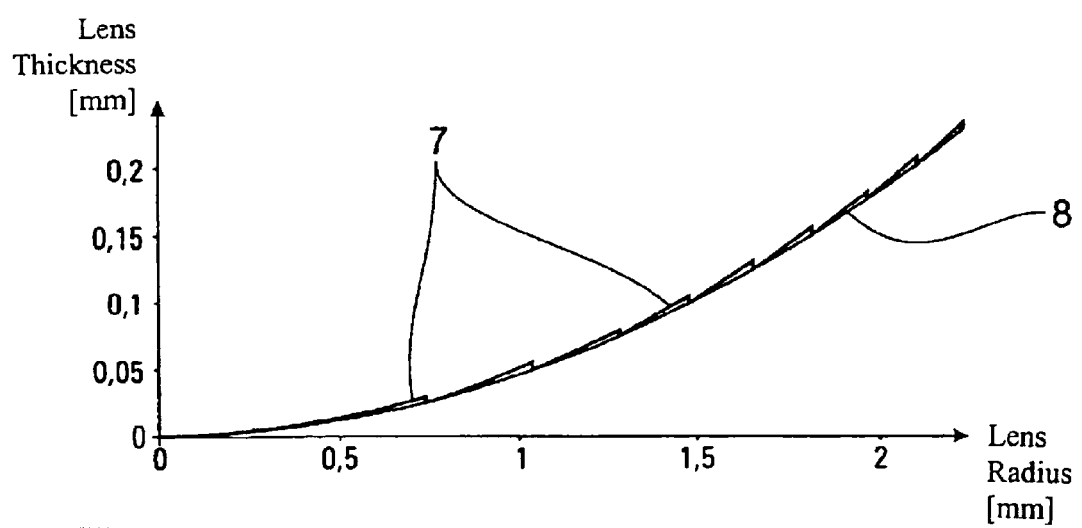
FIG. 2 shows a graphic representation to explain an additional diffractive fine structure, for the forming of a bifocal intraocular lens.

For forming a bifocal lens, an additional diffractive fine structure is provided on the optical lens part 1. This fine structure is preferably formed as a diffractive Fresnel pattern and has the form of annular fine structure elements 7 in sawtooth shape (FIG. 2). FIG. 2 shows the essentially spherical profile of the section curve of the central lens area, forming the refractive component 2, on one side. Starting from a refractive base curve 8, with an essentially spherical section curve profile, the diffractive annular sawtooth zones have tooth depths from 1.5 µm to 2.8 µm. The difference in path length between adjacent zones may be a fraction, for example 0.4 or 0.6, of the design wavelength. The additional diffractive fine structure pattern is preferably provided in the central lens area, forming the refractive component. It may, however, also extend over the annular lens area 3 and overlap the zones located in this area. As FIG. 2 shows, the additional diffractive fine structure elements 7, starting from the refractive base curve 8, are formed into the surface of the lens body, in particular in the central area.

The annular lens area has a width of approximately 0.8 mm to 0.9 mm, in particular 0.8355 mm. The central lens area has a diameter of approximately 4 mm. The central lens area has a smooth surface.

What is claimed is:

1. An intraocular lens comprising:

an optical lens part which has a central lens area having a spherical profile and a diameter of approximately 4 mm, and a single annular lens area surrounding the central lens area, wherein the central lens area and the annular lens area form one common focus;

the annular lens area having concentric annular zones each with a respective optical path of a respective path length, wherein the difference in path length of the optical path between adjacent concentric zones is an integral multiple of n=2 or more of a design wavelength;

the optical lens part having a meridian section provided with an aspherical curvature profile; and the annular area with the concentric zones having the different path lengths being arranged in the lens part in which the aspherical curvature profile has an effect.

2. The intraocular lens as claimed in claim 1, wherein the difference in path length is set by at least one of a selected refractive index of a material or a geometry of the respective zone.

3. The intraocular lens as claimed in claim 1, wherein the annular zones are formed in a sawtooth-like manner.

4. The intraocular lens as claimed in claim 1, wherein the lens has a lens body with opposite front and rear sides and the annular zones are provided on at least one of the front and rear sides of the lens body.

5. The intraocular lens as claimed in claim 1, wherein a reactive component is formed in the central lens area.

6. The intraocular lens as claimed in claim 1, wherein the annular lens area has a width of approximately 0.8 mm to 0.9 mm.

7. The intraocular lens as claimed in claim 6, wherein the annular lens area has a width of 0.835 mm.

8. The intraocular lens as claimed in claim 1, wherein the lens has an outer lens edge with an approximately semicircular cross section.

9. The intraocular lens as claimed in claim 1, wherein the central lens area has a smooth surface.

10. The intraocular lens as claimed in claim 1, wherein the lens is a bifocal lens having additional diffractive zones on the optical lens part.

11. The intraocular lens as claimed in claim 10, wherein the additional diffractive zones are provided on the central lens area, which forms the refractive component.

12. The intraocular lens as claimed in claim 10, wherein the additional diffractive zones are adjacent one another and shaped so that the difference in path length between the adjacent diffractive zones is a fraction of the design wavelength.

13. The intraocular lens as claimed in claim 12, wherein the difference in path length between the adjacent diffractive zones is 0.4 or 0.6 of the design wavelength.

14. The intraocular lens as claimed in claim 13, wherein the design wavelength lies in the green spectral range of visible light.

* * * * *